US005861373A

United States Patent [19]
Gluckman et al.

[11] Patent Number: 5,861,373
[45] Date of Patent: Jan. 19, 1999

[54] IGF-1 TO IMPROVE THE NEURAL CONDITION

[75] Inventors: Peter Gluckman, Reneura, New Zealand; Karoly Nikolics, Belmont, Calif.

[73] Assignee: Genentech, Inc, So. San Francisco, Calif.

[21] Appl. No.: 500,273

[22] Filed: Jul. 10, 1995

Related U.S. Application Data

[63] Continuation of Ser. No. 185,804, filed as PCT/US92/06389, Aug. 3, 1992, published as WO93/02695, Feb. 18, 1993, abandoned.

[30] Foreign Application Priority Data

Aug. 1, 1991 [NZ] New Zealand .............................. 239211

[51] Int. Cl.⁶ .................................................. A61K 38/28
[52] U.S. Cl. .................................................. 514/3; 514/12
[58] Field of Search ............................................ 514/3, 12

[56] References Cited

U.S. PATENT DOCUMENTS 5,093,317  3/1992  Lewis et al. .

FOREIGN PATENT DOCUMENTS

| 308386 | 3/1989 | European Pat. Off. | ....... A61K 37/36 |
| WO 90/14838 | 12/1990 | WIPO | .............................. A61K 37/24 |
| WO 91/02067 | 2/1991 | WIPO | .............................. C12N 15/67 |

OTHER PUBLICATIONS

Beck et al., "Igfl Gene Disruption Results in Reduced Brain Size, CNS Hypomyelination, and Hippocampal Granule and Striatal Parvalbumin–Contatining Neurons" *Neuron* 14:717–730 (Apr. 1995).
Carson et al., "Insulin–like Growth Factor I Increases Brain Growth and Central Nervous System Myelination in Transgenic Mice" *Neuron* 10:729–740 (Apr. 1993).
ffrench–Constant, Charles, "Pathogenesis of multiple sclerosis" *Lancet* 343:271–274 Jan. 29, 1994).
Grinspan et al., "Protein Growth Factors as Potential Therapies for Central Nervous System Demyelinative Disorders" *Annals of Neurology* (Supplement to Volume 36) pp. 140–142 (1994).
Bejar et al., "Anatenatal origin of neurologic damage in newborn infants" *Am. J. Obstet. Gynecol.* 159(2):357–362 (Aug. 1988).
Bohannon et al., "Localization of binding sites for insulin–like growth factor–1 (IGF–1) in the rat brain by quantitative autoradiography" *Brain Research* 444:205–213 (1988).
Bondy et al., "Cellular pattern of type–1 insulin–like growth factor receptor gene expression during maturation of the rat brain: comparison with insulin–like growth factors I and II" *Neurosci.* 46(4):909–923 (1992).
Brownstein et al. *Handbook of Chemical Neuroanatomy, Classical Transmitters in the CNS*, Bjorklund et al., Elsevier, Amsterdam pp. 23–54 (1984).

Gluckman et al., "A role for IGF–1 in the rescue of CNS neurons following hypoxic–ischemic injury" *Biochem. & Biophys. Res. Comm.* 182(2):593–599 (Jan. 31, 1992).
Guler et al., "Effects of recombinant insulin–like growth factor I on insulin secretion and renal function in normal human subjects" *Proc. Natl. Acad. Sci. USA* 86:2868–2872 (Apr. 1989).
Guler et al., "Short–term metabolic effects of recombinant human insulin–like growth factor I in healthy adults" *New England J. of Medicine* 317(3):137–140 (Jul. 16, 1987).
Hill et al., "Autoradiographic Localization of Insulin Receptors in Rat Brain: Prominence in Olfactory and Limbic Areas" *Neurosci.* 17(4):1127–1138 (1986).
Kanje et al., "Insulin–like growth factor I (IGF–1) stimulates regeneration of the rat sciatic nerve" *Brain Research* 486:396–398 (1989).
Kiess et al., "Rat C6 Glial Cells Synthesize Insulin–Like Growth Factor I (IGF–I) and Express IGF–I Receptors and IGF–II/Mannose 6–Phosphate Receptors" *Endocrinology* 124(4):1727–1736 (1989).
Knusel et al., "Selective and Nonselective Stimulation of Central Cholinergic and Dopaminergic Development in vitro by Nerve Growth Factor, Basic Fibrablast Growth Factor, Epidermal Growth Factor, Insulin and the Insulin–like Growth Factors I and II" *J. Neurosci.* 10(2):558–570 (Feb. 1990).
Lesniak et al., "Receptors for Insulin–like Growth Factors I and II: Autoradiographic Localization in Rat Brain and Comparison to Receptors for Insulin" *Endocrinology* 123(4):2089–2099 (1988).
McMorris et al., "Insulin–Like Growth Factor I Promotes Cell Proliferation and Oligodendrogilial Commitment in Rat Glial Progenitor Cells Developing In Vitro" *J. Neurosci. Res.* 21:19–209 (1988).
McMorris et al., "Insulin–like growth factor I/somatomedin C: A potent inducer of oligodendrocyte development" *Proc. Natl. Acad. Sci. USA* 83:822–826 (Feb. 1986).
Mesulam et al., "Atlas of Cholinergic Neurons in the Forebrain and Upper Brainstem of the Macaque Based on Monoclonal Choline Acetyltransferase Immunohistochemistry and Acetylcholinesterase Histochemistry" *Neurosci.* 12(3):669–686 (1984).

(List continued on next page.)

*Primary Examiner*—Paul J. Killos
*Attorney, Agent, or Firm*—Walter H. Dreger; Flehr Hohbach Test Albritton & Herbert LLP

[57] ABSTRACT

A method of treating injuries to or diseases of the central nervous system that predominantly affects glia and/or non-cholinergic neuronal cells characterized in that it comprises the step of increasing the active concentration(s) of insulin-like growth factor 1 and/or analogues thereof in the central nervous system of the patient. The present invention also provides therapeutic compositions comprising insulin-like growth factor 1 and/or analogues thereof for administration to a patient at or following a neural insult, which compositions are useful in minimizing damage to the central nervous system that would otherwise occur following the insult.

1 Claim, 6 Drawing Sheets

OTHER PUBLICATIONS

Mozell et al., "Insulin–Like Growth Factor I Stimulates Oligodendrocyte Development and Myelination in Rat Brain Aggregate Cultures" *J. Neurosci. Res.* 30:382–390 (1991).

Philipps et al.. "The Effects of Biosynthetic Insulin–Like Growth Factor–1 Supplementation on Somatic Growth, Maturation, and Erythropoiesis on the Neonatal Rat" *Pediatric Res.* 23(3):298–305 (1988).

Scheiwiller et al., "Growth restoration of insulin–deficient diabetic rats by recombinant human insulin–like growth factor I" *Nature* 323:169–171 (Sep. 11 1986).

Sinha et al., "Ischaemic brain lesions diagnosed at birth in preterm infants: clinical events and developmental outcome" *Arch. Dis. Child.* 65:1017–1020 (1990).

Skottner et al., "Growth Responses in a Mutant Dwarf Rat to Human Growth Hormone and Recombinant Human Insulin–Like Growth Factor I" *Endocrinology* 124(5):2519–2526 1989).

Skottner et al., "Recombinant human insulin–like growth factor: testing the somatomedin hypothesis in hypophysectomized rats" *J. Endocr.* 112:123–132 (1987).

Sturm et al., "Insulin–Like Growth Factor Receptors and Binding Protein in Rat Neuroblastoma Cells" *Endocrinology* 124(1):388–396 (1989).

Svrzic et al., "Insulin–like growth factor 1 supports embryonic nerve cell survival" *Biochem. & Biophys. Res. Comm.* 172(1):54–60 (Oct. 15, 1990).

Tanner et al., "Comparative rapidity of response of height, limb muscle, and limb fat to treatment with human growth hormone in patients with and without growth hormone deficiency" *Acta Endrocrinologica* 84:681–696 (1977).

Uthne et al., "Effects of Human Somatomedin Preparations on Membrane Transport and Protein Synthesis in the Isolated Rat Diaphragm" *J. Clin. Endocrinol. Metab.* 39(3):548–554 (1974).

van Buul–Offers et al., "Biosynthetic Somatomedin C(SM–C/IGF–I) Increases the Length and Weight of Snell Dwarf Mice" *Pediatr. Res.* 20(9):825–827 (1986).

Werther et al., "Localization of Insulin–Like Growth Factor–I mRNA in Rat Brain by in Situ Hybridization—Relationship to IGF–I Receptors" *Mol. Endocrinol.* 4(5):773–778 (1990).

Yamaguchi et al., "Increase of extracellular insulin–like growth factor I (IGFI) concentration following electrolytical lesion in rat hippocampus" *Neuroscience Letters* 128:373–276 (1991).

Young et al., "Selective Reduction of Blood Flow to White Matter During Hypotension in Newborn Dogs: A Possible Mechanism of Preiventricular Leukomalacia" *Ann. Neurol.* 12(5):445–448 (Nov. 1982).

72 hrs     120 hrs
FIG. IA
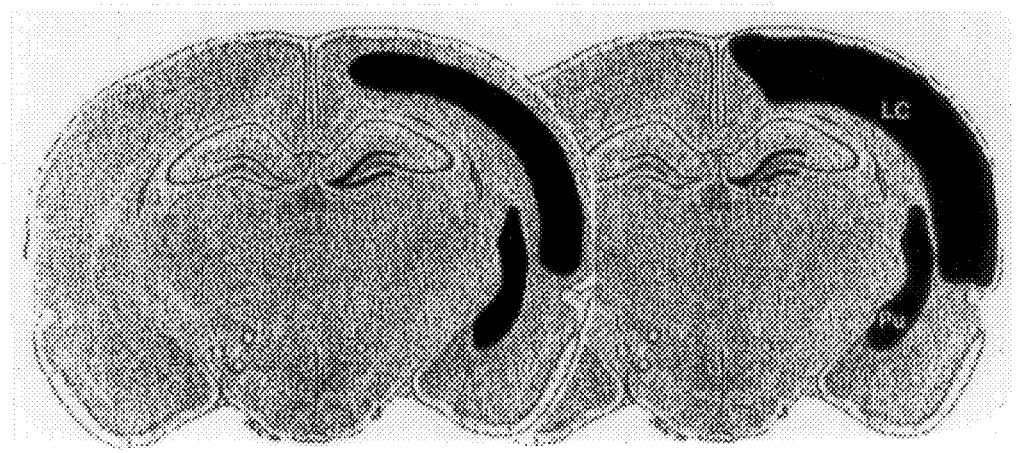
72 hrs     120 hrs
FIG. IB

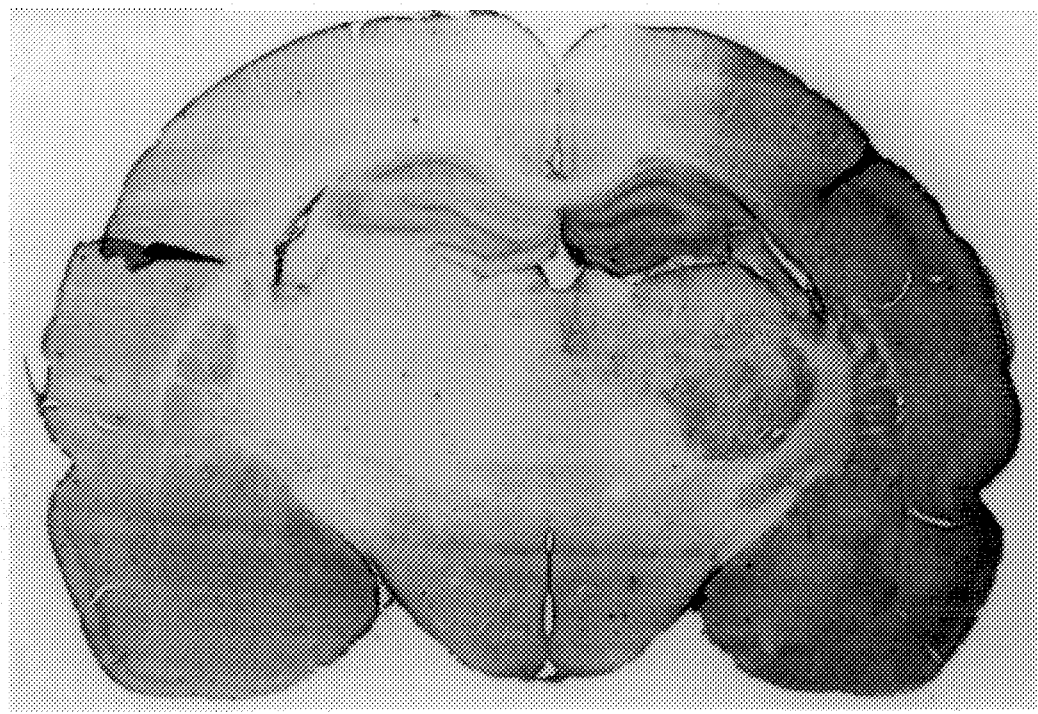
FIG. IC
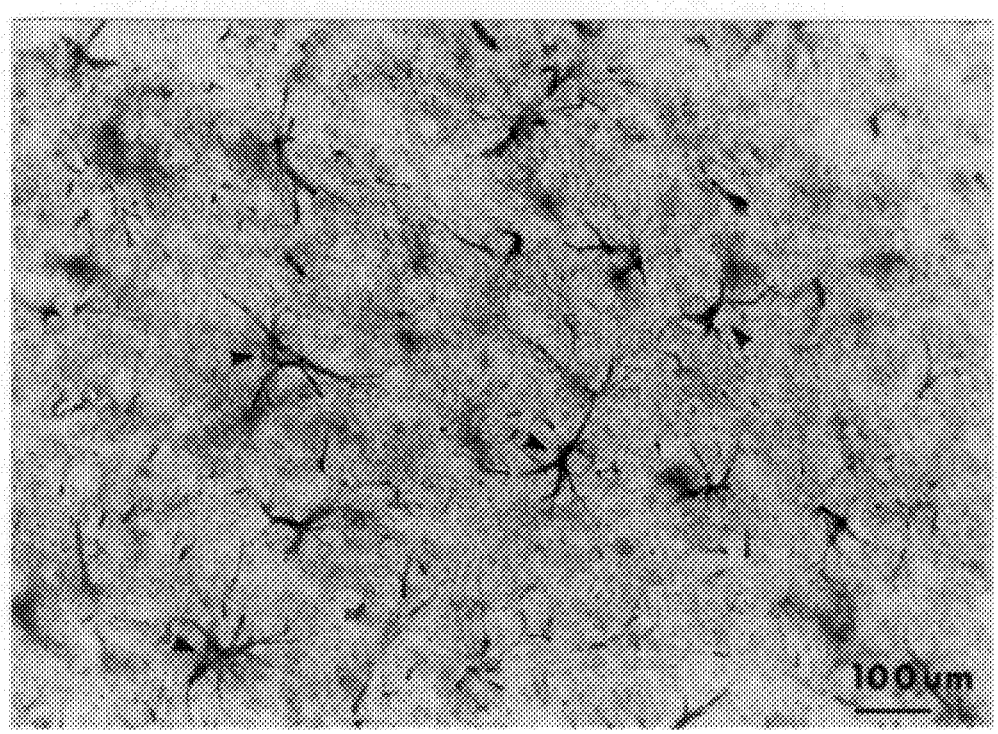
FIG. ID

IGF-1 TO IMPROVE THE NEURAL CONDITION

This is a continuation of applications Ser. No. 08/185,804 filed Jan. 28, 1994, now abandoned, which is a 35 USC § 371 of PCT/US92/06389 filed on Aug. 3, 1992, and International Application 239211 in New Zealand filed on Aug. 1, 1991 which designated the U.S., which applications are incorporated herein by reference and to which applications priority is claimed under 35 USC § 120.

FIELD OF THE INVENTION

This invention relates to methods and therapeutic compositions for the treatment or prevention of central nervous system (CNS) damage and relates particularly although not necessarily to a method of increasing the concentration of insulin-like growth factor 1 (IGF-1) in the central nervous system of the patient to treat an injury or disease that primarily causes damage to glia and/or other non-cholinergic cells of the CNS.

BACKGROUND OF THE INVENTION

After asphyxial, traumatic, toxic, infectious, degenerative, metabolic, ischemic or hypoxic insults to the central nervous system (CNS) of man a certain degree of damage in several different cell types may result. For example periventricular leucomalacia, a lesion which affects the periventricular oligodendrocytes is generally considered to be a consequence of hypoxicischemic injury to the developing preterm brain (Bejar et al., *Am. J. Obstet. Gynecol.,* 159:357–363 (1988); Sinha et al., *Arch. Dis. Child.,* 65:1017–1020 (1990); Young et al., *Ann. Neurol.,* 12:445–448 (1982)). Further cholinergic neuronal cell bodies are absent from most regions of the cortex in primates (Mesulam et al., *Neurosci.,* 12:669–686 (1984)) and rats (Brownstein et al. in *Handbook of Chemical Neuroanatomy, Classical Transmitters in the CNS,* Bjorklund et al., eds., Elsevier, Amsterdam, pp. 23–53 (1984)). Damage to the cerebral cortex by trauma, asphyxia, ischemia, toxins or infection is frequent and may cause sensory, motor or cognitive deficits. Glial cells which are non-neuronal cells in the CNS are necessary for normal CNS function. Infarcts are a principle component of hypoxicischemic induced injury and less of glial cells is an essential component of infarction.

Diseases of the CNS also may cause loss of specific populations of cells. For example multiple sclerosis is associated with loss of myolin and oligodendrocytes, similarly Parkinson's disease is associated with loss of dopaminergic neurons. Some situations in which CNS injury or disease can lead to predominant loss of glia or other non-cholinergic cell types or infarction include: perinatal asphyxia associated with fetal distress such as following abruption, cord occlusion or associated with intrauterine growth retardation; perinatal asphyxia associated with failure of adequate resuscitation or respiration; severe CNS insults associated with near miss drowning, near miss cot death, carbon monoxide inhalation, ammonia or other gaseous intoxication, cardiac arrest, collapse, coma, meningitis, hypoglycaemia and status epilepticus; episodes of cerebral asphyxia associated with coronary bypass surgery; cerebral anoxia or ischemia associated with stroke, hypotensive episodes and hypertensive crises; cerebral trauma.

There are many other instances in which CNS injury or disease can cause damage to glia and non-cholinergic neurons of the CNS. It is desirable to treat the injury in these instances. Also, it is desirable to prevent or reduce the amount of CNS damage which may be suffered as a result of induced cerebral asphyxia in situations such as cardiac bypass surgery. To date, there has been no reference in the prior art to the manipulation of insulin-like growth factor 1 (IGF-1) to prevent or treat CNS injury or disease leading to infarction or loss of glia and other non-cholinergic neuronal cells in vivo.

IGF-I is a polypeptide naturally occurring in human body fluids, for example, blood and human cerebral spinal fluid. Most tissues, and especially the liver, produce IGF-I together with specific IGF-binding proteins. IGF-I production is under the dominant stimulatory influence of growth hormone (GH), and some of the IGF-I binding proteins are also increased by GH. See Tanner et al., *Acta Endocrinol.,* 84: 681–696 (1977); Uthne et al., *J. Clin. Endocrinol. Metab.,* 39: 548–554 (1974)). IGF-I has been isolated from human serum and produced recombinantly. See, e.g., EP 123,228 and 128,733.

Various biological activities of IGF-I have been identified. For example, IGF-I is reported to lower blood glucose levels in humans. Guler et al., *N. Engl. J. Med.* 317: 137–140 (1987). Additionally, IGF-I promotes growth in several metabolic conditions characterized by low IGF-I levels, such as hypophysectomized rats [Skottner et al., *J. Endocr.,* 112: 123–132 (1987)], diabetic rats [Scheiwiller et al., *Nature,* 323: 169–171 (1986)], and dwarf rats [Skottner et al., *Endocrinology* 124: 2519–2628 (1989)]. The kidney weight of hypophysectomized rats increases substantially upon prolonged infusions of IGF-I subcutaneously. Guler et al., *Proceedings of the 1st European Congress of Endocrinology,* 103: abstract 12–390 (Copenhagen, 1987). The kidneys of Snell dwarf mice and dwarf rats behaved similarly. van Buul-Offers et al., *Pediatr. Res.,* 20: 825–827 (1986); Skottner et al., *Endocrinology,* supra. An additional use for IGF-I is to improve glomerular filtration and renal plasma flow. Guler et al., *Proc. Natl. Acad. Sci. USA,* 86: 2868–2872 (1989). The anabolic effect of IGF-I in rapidly growing neonatal rats was demonstrated in vivo. Philipps et al., *Pediatric Res.,* 23: 298 (1988). In underfed, stressed, ill, or diseased animals, IGF-I levels are well known to be depressed.

IGF-1 is thought to play a paracrine role in the developing and mature brain (Werther et al., *Mol. Endocrinol.* 4:773–778 (1990)). In vitro studies indicate that IGF-1 is a potent non-selective trophic agent for several types of neurons in the CNS (Knusel et al., *J. Neurosci.,* 10(2):558–570 (1990); Svezic and Schubert, *Biochem. Biophys. Res. Commun.,* 172(1):54–60 (1990)), including dopaminergic neurons (Knusel et al., *J. Neurosci.,* 10(2):558–570 (1990)) and oligodendrocytes (McMorris and Dubois, *J. Neurosci. Res.* 21:199–209 (1988); McMorris et al., *PNAS, USA,* 83:822–826 (1986); Mozell and McMorris, *J. Neurosci. Res.* 30:382–390 (1991)). Methods for enhancing the survival of cholinergic neuronal cells by administration of IGF-1 have been described (Lewis, et al., U.S. Pat. No. 5,093,317 (issued Mar. 3, 1992)).

IGF-1 receptors are wide spread in the CNS (Bohannon et al., *Brain Res.,* 444:205–213 (1988); Bondy et al., *Neurosci.,* 46:909–923 (1992)) occurring on both glia (Kiess et al., *Endocrinol.,* 124:1727–1736 (1989)) and neurons (Sturm et al., *Endocrinol.,* 124:388–396 (1989)). These receptors mediate the anabolic and somatogenic effects of IGF-1 and have a higher affinity for IGF-1 compared to insulin (Hill et al., *Neurosci.,* 17:1127–1138 (1986); Lesniak et al., *Endocrinol.,* 123:2089–2099 (1988)). From 3 days after injury greatly increased levels of IGF-1 are produced particularly in the developing CNS (Gluckman et al., *Biochem.*

Biophys. Res. Commun., 182(2);593–599 (1992); Yamaguchi et al., *Neurosci. Lett.* 128:273–276 (1991)). The effect of IGF-1 as a central neuroprotectant when administered after an insult (Gluckman et al., *Biochem. Biophys. Res. Commun.,* 182(2);593–599 (1992)) (see experiments A and B) suggests a mode of action involving interference with the activated processes leading to cell death. Endogenous and exogenous IGF-1 stimulate peripheral nerve regeneration (Karje et al., *Brain Res.,* 486:396–398 (1989)). IGF-1 has been shown to enhance ornithine decarboxylase activity in normal rat brains (U.S. Pat. No. 5,093,317).

It is an object of the invention to provide a method and/or medicament (therapeutic composition) for treating or preventing CNS damage which will go at least some way to meeting the foregoing desiderata in a simple yet effective manner or which will at least provide the public with a useful choice.

SUMMARY OF THE INVENTION

Accordingly, in a first aspect the invention consists in a method of treating neural damage suffered after a CNS insult characterised in that it comprises the step of increasing the active concentration(s) of IGF-1 and/or analogues of IGF-1 in the CNS of the patient.

In particular, the concentration of IGF-1 in the CNS of the patient is increased.

The term "treat" when used herein refers to the effecting of a reduction in the severity of the CNS damage, by reducing infarction, and loss of glial cells and non-cholinergic neuronal cells, suffered after a CNS insult. It encompasses the minimising of such damage following a CNS insult.

Preferably, IGF-1 and/or analogues thereof are administered to the patient directly.

Alternatively, a compound may be administered which upon administration to the patient, increases the active concentration of IGF-1 or naturally occurring analogues of IGF-1 in the CNS of the patient. For example, positively regulating binding proteins of IGF-1, or naturally occurring analogues thereof may be administered.

Preferably, the medicament is administered in the period from the time of injury to 100 hours after the CNS insult and more preferably 0.5 to 8 hours after the CNS insult.

In a first form, preferably, said IGF-1 and/or an analogue or analogues thereof selected from the group; IGF-2, truncated IGF-1 (des 1–3 IGF-1), analogues of IGF-2, and synthetic analogues of IGF-1, is administered by lateral cerebro ventricular injection into the brain of a patient in the inclusive period from the time of the CNS insult to 8 hours thereafter.

In another preferred form, IGF-1 and/or an analogue or analogues thereof selected from the group; IGF-2, truncated IGF-1 (des 1–3 IGF-1), analogues of IGF-2, and synthetic analogues of IGF-1, is administered through a surgically inserted shunt into the cerebro ventricle of a patient in the inclusive period from the time of the CNS insult to 8 hours thereafter. In another preferred form of the present invention, IGF-1 and/or an analogue or analogues thereof selected from the group; IGF-2, truncated IGF1 (des 1–3 IGF-1), analogues of IGF-2, and synthetic analogues of IGF-1, is administered peripherally into a patient for passage into the lateral ventricle of the brain in the inclusive period of from the time of the CNS insult to 8 hours thereafter. Preferably, it is IGF-1, itself, that is administered by way of lateral cerebro ventricle injection or by use of the surgically inserted shunt.

Preferably the medicament is administered according to the pattern of injury or time lapsed after a CNS insult.

Preferably the dosage range administered is from about 0.1 to 1000 $\mu$g of IGF-1 or said analogue or said compound that elevates the concentration thereof per 100 gm of body weight.

IGF-1 may be used alone or in conjunction with other medicaments or growth factors designed to ameliorate against loss of CNS cells such as glia and non-cholinergic neurons.

By "prevent" is meant a reduction in the severity of CNS damage suffered after a CNS insult and may also include inhibition of the symptoms of CNS damage.

In yet a further aspect, the invention the use of IGF-1 and/or analogues thereof in the preparation of a medicament for treating CNS damage.

Alternatively, the invention comprises the use of a compound which, upon administration to a patient, increases the active concentration of IGF-1 and/or naturally occurring analogues thereof in the CNS of the patient in the preparation of a medicament for treating injury to the CNS.

The invention also consists in a medicament suitable for treating CNS damage suffered after a CNS insult comprising IGF-1, and/or analogues thereof optionally provided in a pharmaceutically acceptable carrier or diluent.

The medicament for treating CNS damage may also comprise a compound which, upon administration to the patient suffering CNS damage, increases the active concentration of IGF-1 and/or naturally occurring analogues thereof in the CNS of said patient.

Although the present invention is defined broadly above, it will be appreciated by those skilled in the art that it is not limited thereto but includes embodiments of which the description provides examples.

BRIEF DESCRIPTION OF DRAWINGS

A better understanding of the invention will be gained from reference to the foregoing examples and drawings wherein:

FIG. 1 shows composite drawings (A–D) illustrating the distribution of IGF-1 mRNA, IGF-1 peptide and BP-3 mRNA following severe ischemic hypoxia.

DESCRIPTION OF THE PREFERRED EMBODIMENTS

Figure 2:
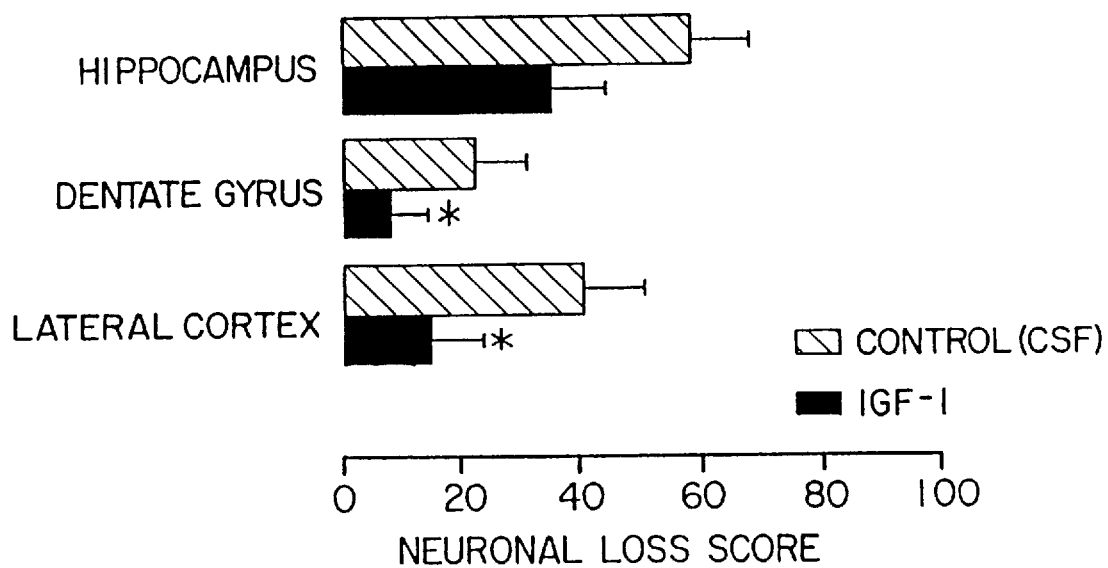
FIG. 2 is a histogram illustrating the neuronal loss for IGF1 treated and control rats in Experiment 1, in which IGF-1 20 $\mu$g was administered 2 hrs following ischemic-hypoxia.

The invention relates to a method of manipulating neural damage. In a first aspect, the invention relates to a method of treating CNS damage after an insult to the CNS. For example, the patient may have suffered perinatal asphyxia or asphyxia or cerebral ischemia associated with a stroke or other non-limiting examples of CNS insults having been described earlier herein. In these instances, it is desirable to reduce or eliminate the symptoms of CNS damage.

CNS damage may for example be measured by the degree of permanent neurological deficit cognitive function, and/or propensity to seizure disorders.

It is proposed that the concentration of IGF-1 and/or analogues thereof in the CNS and in the brain of the patient in particular should be increased in order to treat the CNS damage. Accordingly, IGF-1 and/or analogues thereof can be administered directly to the patient. By IGF-1 is meant insulin-like growth factor 1. By analogues of IGF-I is meant compounds which exert a similar biological effect to IGF-1 and includes IGF-2 and analogues of IGF-2 (IGF-2 is known to exert some similar biological effects to IGF-1), naturally occurring analogues (e.g. des. 1–3 IGF-1) or any of the known synthetic analogues, of IGF-1. These compounds can be derived from humans or other animals. IGF-1 and analogues can he purified from natural sources or produced by recombinant DNA techniques. Recombinant IGF-1 and des 1–3 IGF-1 can be obtained commercially.

Alternatively, compounds can be administered which, upon administration to the patient, increase the active concentration of IGF-1 and/or naturally occurring analogues thereof in the CNS. By "active concentration" is meant the biological concentration of IGF-1 and/or analogues in the CNS of the patient able to exert an effect on CNS damage. For example, positively regulating binding proteins of IGF-1 may be used to elevate the active concentration of IGF-1. IGF-1 binding proteins 1 to 3 (IGF-1 BP1–3) may for example elevate the concentration of IGF-1 in the CNS under appropriate conditions.

IGF-1, analogues thereof and compounds which elevate the active concentrations thereof can be administered centrally or systemically. Desirably, the compositions are administered directly to the CNS of the patient. Accordingly, the compositions may be administered directly into the brain or cerebrospinal fluid by techniques including lateral ventricular through a burrhole or anterior fontenelle, lumbar or cisternal puncture or the like.

If desired, a combination of the compounds can be administered. In addition they may be readministered with other agents or growth factors, for example, transforming growth factor beta (TGF-β).

The foregoing experiments show that the expression of IGF-1 after a neural insult follows a specified time course and occurs in specified areas of the body. Accordingly, the compositions should be administered according to the pattern of CNS injury and time lapsed subsequent to an insult so as to produce the most desirable results. The compositions may be administered directly to the region of the body where the greatest CNS damage has occurred.

The compositions may for example be administered about 0.5 to 100 hours after an insult. only one treatment may be necessary. Alternatively, repeated treatment may be given to the patient.

A suitable dosage range may for example be between about 0.1 to 1000 µg of IGF-1 and/or analogues or compounds that elevate the concentrations thereof per 100 gm of body weight where the composition is administered centrally.

The invention also relates to a medicament for treating CNS injury. The medicament can comprise IGF-1 and/or analogues thereof or a compound which elevates the concentration of IGF-1 in the CNS such as IGF-1 binding proteins 1 to 3 or a mixture of these. The compounds are desirably provided in a pharmaceutically acceptable carrier or diluent such as those known in the art. IGF-1, IGF-2, analogues and compounds that elevate the concentration thereof can be manufactured by recombinant DNA techniques such as those disclosed in New Zealand Patent Number 208339 where the respective DNA sequences are known. Alternatively, the compounds can be isolated from natural sources.

The invention is supported by the following experimental data. In the following studies it was found that:

1) IGF-1 is expressed after a CNS insult over a defined time course in specific regions of injury.
2) Alterations in CNS levels of IGF-1 can alter CNS damage resulting as a consequence of an insult to the CNS.
3) IGF-1 administered after an insult to the CNS improves outcome whereas IGF-1 administered prior to an insult does not worsen the result. Thus, the effect of treatment with IGF-1 depends on its temporal relationship to the insult.

Twenty one day old rats were subjected to unilateral carotid ligation followed by inhalational asphyxia under defined conditions to produce either mild or severe neuronal loss with infarction on the ligated side.

Mild or severe neuronal loss was induced in 21 day rats as follows: The right carotid artery was ligated under light halothane anaesthesia. They were then placed in an incubator at 34° C. and 85% humidity. The inspired gases were replaced by 8% $O_2$ in nitrogen for 15 min (mild) or 90 min (severe) then returned to air. At various times after hypoxia (1 hr, 5 hrs, 3 and 5 days) the animals were anaesthetized with pentobarbitone (Nembutal), the brains-removed and snap frozen on dry ice for in situ hybridization. For histology, rats were sacrificed 5 days after hypoxia and then perfused with 0.9% saline followed by formaldehyde-acetic acid-methanol (1:1:8).

At defined times after the asphyxia the rats were sacrificed for histology. After 90 min asphyxia (severe) neuronal loss assessed by thionine/acid fuchsin stain was widespread within the ligated cortex. There was severe loss of neurons and infarction in the middle cerebral artery territory, including the lateral cortex, hippocampus, striatum and thalamus. In situ hybridisation histochemistry was performed using a mouse IGF-1 cDNA probe derived from a genomic clone which includes the entire sequence for exon 3.

Hybridization histochemistry was performed as described elsewhere in McCabe, J. T., Morrell, J. L, Ivel, R., Schmale, H. Richter, D. Pfaff, D. W. In situ hybridization technique to localise rRNA and mRNA in mammalian neurons, *J. Histochem. Cytochem.* 34 (1986) 45–50; Smith, M., Auer, R., Siesjo, B., The density and distribution of ischemic brain injury in the rate following 2–10 min of forebrain ischemia, *Ann. Neuropathol.* 64 (1984) 319–332; Mathews, L. S. Norstedt, G., Palmiter, R. D. (1986) Regulation of insulin-like growth factor I gene expression by growth hormone, *Proc. Natl. Acad. Sci.* USA 83:9343–9347; Lowe, W. L. Jr., Roberts, C. T. Jr., Lasky, S. R. LeRoith, D. (1987) Differential expression of alternative 5'untranslated regions in mRNAs encoding rat insulin-like growth factor I, *Proc. Natl. Aced. Sci.* USA 84:8946–8950.

After hybridization the sections were washed 4 times in 2×SSC plus 10 mM B-mercaptoethanol at room temperature for 10 minutes each, 4 times in 2×SSC at room temperature for 10 minutes each, twice in 2×SSC at 50° C. for 15 minutes each and twice in 0.2×SSC at 50° C. for 10 minutes each. For IGF-1 MRNA detection an 830 bp mIGF-1 DNA probe derived from a genomic mouse spleen DNA library was used. The probe includes the entire sequence of exon 3 (182 bp). The murine IGF-1 probe was kindly donated by Dr P. Rotwein, Department International Medicine, Washington University, (St. Louis, Mo. 63110). For IGFBP-1 mRNA detection a 364 bp fragment of hIGFBP-1 was used containing the sequence for most of the c-terminus of the protein and a small amount of the 3'-flanking sequence. The hIGFBP-1 probe was kindly donated by Dr. D. R. Clemmons Department Medicine University North Carolina at Chapel Hill (Chapel Hill, N.C. 27599-7170, USA). For IGFBP-3 mRNA detection a full length hIGFBP-3 cDNA of about 2.6 kb was used which was kindly donated by Dr. S. K.-Spratt (Biogrowth Inc., Richmond, Calif. 94806, USA). Controls were performed using RNAase A (40 µg/ml 0.5M NaCl/20 mM Tris 7.5/1 mM EDTA at 37° C. RNAase pretreatment almost entirely depressed the signal Northern blots an each probe revealed the anticipated bands at 7.4, 1.9 and 1.7-1.1 kb for IGF-1, a single band for IGFBP-3 at 2.6 kb, the major band for BP-1 was at 1.7 kb.

The results of this experiment are illustrated in FIG. 1.

The resulting signal showed an induction of the IGF-1 MRNA by 72 hours. The induction was primarily restricted to the ligated side and was most marked after 5 days in the lateral cortex, hippocampus, striatum, thalamus and pyriform cortex (see FIG. 1).

In FIG. 1, the right hemisphere always represents the damaged side. Panels A and B show diagrammatic representations of the distribution of MRNA for IGF-1(A), and IGFBP-3(B), at 72 and 120 hours following asphyxia. Twenty-one day old rats were subject to unilateral carotid ligation plus 90 min of inhalational asphyxia under standard conditions. In situ hybridization was performed on 12 µm sections using conditions of moderately high stringency (see above).

Panel C shows anti-hIGF-1 immunohistochemistry 120 hours following asphyxia. IGF-1 immunohistochemistry was done as follows: The anti-serum used (878/4) was raised to rec n-met hIGF-1 and had a cross reactivity with IGF-2 of <1%. The IGF-1 was detected using standard immunocytochemical methods. For double labelling reactions, we first incubated brain sections with rabbit anti-hIGF-1 and developed this reaction with the chromogen diaminobenzedine, which gives a brown reaction product. Then after washing, sections were incubated with monoclonal antibodies to glial fibrillary acidic protein (GFAP, Amersham) and this second reaction was visualised with the chromogen benzidine dihydrochloride, which gives a blue reaction product. With this method we discovered that IGF-1 positive cells were also GFAP-positive and were therefore astrocytes. The staining was markedly reduced by preabsorption with hIGF1.

Panel D is a high power magnification of panel C. It shows the hippocampal region of the damaged side. Astrocyte-like calls (arrows), as confirmed by GFAP double labelling (not shown), express IGF-1 after insult. The magnifications are indicated in the panels.

KEY:
DG=dentate gyrus
LC=Lateral cortex
Pu=Putamen
Th=Thalamus.

The specificity of the induction was demonstrated by predominately unilateral expression on the ligated side, lesser induction in animals subjected to a lesser insult and by negative controls using RNAse A. The probe was also used to hybridize a Northern blot of rat liver poly(A)'RNA samples. The bands detected after hybridization to the MIGF-1 probe are in agreement with the data reported in the literature [S. Shimasasi, A. Koba, M. Mecado, M. Shimonasa, N. Ling, *Biochem. Biophys. Res. Comm.* 165, 907 (1989)].

Immunohistochemistry was performed using a rabbit anti-h IGF-1 polydonal anti-serum. Cells staining for IGF-1 could be identified throughout the cerebrum bilaterally but the intensity of the staining was considerably greater in the damaged region on the ligated hemisphere. This staining was seen in GFAP-positive astrocytes (see FIG. 1).

In the circulation and within tissues, IGF-1 is generally associated with specific binding proteins. The cerebrospinal fluid has relatively high concentrations of the IGF-2 specific binding protein IGFBP-2 but low levels of the IGF-1 binding proteins IGFBP-3 or IGFBP-1 [L. Tseng, A. Brown, Y. Yang, J. Romanus, C. Orlowski, T. Taylor, M. Rechler, *Mol Endo* 3, 1559 (1989); CSF BPs and BPs in general].

While the significance of these binding proteins remains controversial they clearly alter the biological availability and response to IGF-1 in a specific manner. Further, as IGFBP-1 and IGFBP-3 are independently regulated, it is likely they subserve different biological significance. The expression of IGFBP-3 and IGFBP-1 was examined using in situ hybridization histochemistry. No IGFBP-3 mRNA as detectable in brains of control rats (21 days p.p.). Following the hypoxic-ischemic injury a signal for the IGFBP-3 mRNA was apparent in the injured region by 72 hours after the insult and maximal at 120 hours. The induction was confined to the lateral cerebral cortex, striatum and dentate gyrus. No induction was seen in the contralateral cortex.

In contrast, preliminary data suggest a low expression of IGFBP-1 mRNA in the contralateral hemisphere early after the insult (+1 hr). No IGFBP-1 mRNA could be found in the controls or at any other time points after hypoxia examined so far.

These data suggest that following an hypoxic ischemic insult IGF-1 is induced in astrocytes, particularly in the area of damage and that there it an altered milieu of binding proteins with a greater BP-3 to BP-1 ratio.

It has been suggested that the primary form of IGF-1 in the CNS is a truncated form with a N-terminal tripeptide missing [V. Sara, C. Carlsson-Skwirut, T. Bergman, H. Jorvall, P. Roberts, M. Crawford, L. Hakansson, L. Civalero, A. Nordberg, *Biochem Biophys Res Comm* 165, 766 (1989); des 1–3 IGF-1). This truncated IGF-1 is believed to be formed by a different cleavage from pro-IGF-1. The antibody used does not distinguish des 1–3-IGF-1 from IGF-1. Des 1–3 IGF-1 has little binding to IGFBP-1 but relatively maintained binding to IGFBP-3. It is of interest that the changes we have observed are compatible with this binding profile and suggest that IGF-1 complexed to IGFBP-3 may have a particular role in the post asphyxial brain.

The present invention is further illustrated by the following examples. These examples are offered by way of illustration only and are not intended to limit the invention in any manner. All patent and literature references cited throughout the specification are expressly incorporated.

EXAMPLE 1

The objective of these studies was to assess the effects of administering IGF-1 after a CNS insult. Adult rats (200–300 gm) were used. The experiments involved treating the rats with IGF-1 before and after a CNS insult. These rats had an hypoxic-ischemic insult to one cerebral hemisphere induced in a standard manner. One carotid artery was ligated and the animal was subjected two hours later to a defined period of inhalational hypoxia. The degree, length of hypoxia, ambient temperature and humidity were defined to standardise the degree of damage. They were sacrificed five days later for histological analysis using stains (acid-fuchsin) specific for necrotic neurons.

In such experiments cell death typically is restricted to the side of the side of arterial ligation and is primarily in the hippocampus, dentate gyrus and lateral cortex of the ligated hemisphere.

Experiment A

Unilateral hypoxic-ischemic injury was induced in adult 300±10 g) male Wistar rats. The rats underwent unilateral carotid ligation under right halothane anaesthesia. Following one hour recovery they were placed in an incubator at 31° C. and 85±5% humidity for one hour before insult. They were subjected to 10 min. inhalational asphyxia (FiO2 6.0%) and maintained in the incubator for one hour after asphyxia.

Two hours after the termination of the inhalational insult, a single stereotaxically controlled lateral cerebroventricular injection of either 20 μg recombinant human IGF-1 or artificial cerebrospinal fluid (CSF) was given.

Recombinant hIGF-1 or diluent was prepared and administered to weight matched pairs as follows: Two hours after asphyxia the rats were given a light halothane anaesthatic, placed in a stereotaxic frame and a single ICV injection of either 10 μl of CSF (n=14) or 10 μl of CSF plus 20 μg IGF-1 (n=14) was given. Recombinant hIGF-1 (Genentech, South San Francisco) was dissolved in the CSF diluent comprising 0.1M acetic acid at 200 μg/10 μl. This solution was diluted 9 times with 0.15M PBS (Phosphate buffered saline) giving a pH of 7.3±0.5

The animals were then maintained for 120 hrs, anaesthetized and the brains fixed in situ with formal dehyde-acetic acid-methanol (1:1:8) for histological assessment.

Surviving and dead neurons were discriminated with the use of an thionin/acid fuschin staining technique [C. Williams, A. Gunn, C. Mallard, P. Gluckman *Ped Res*, (1990). A. Brown, J. Brierley, *J Neural Sci* 16 59–84 (1971)].

The degree of neural damage suffered was quantified by measuring the neuronal loss score. The neuronal loss scores are the average from the susceptible regions of the hippocampus and cerebral cortex—100% equals total loss of neurones, 0% equals 0 loss.

The percentage of dead neurons was estimated by two independent observers, one of whom was blinded to the experiment. The correlation between scores obtained by the two observers was r=0.92 p,0.0001. The effect of treatment was evaluated with MANOVA followed by pair wise comparisons of each region using Fisher's least-significant-difference procedure. Treatment reduced neuronal loss ($p<0.01$). Neuronal loss was reduced in the dentate gyrus and lateral cortex (*$p<0.05$). There were no significant differences between IGF-1 and CSF treated groups for the following physiologic parameters: mass, age, venous glucose and lactate concentrations and mean cortical temperature during hypoxia.

The results are shown in FIG. 2. IGF-1 therapy reduced the extent of neuronal death in the ligated hemisphere compared to the CSF-treated controls. Systemic blood glucose did not change in response to intracerebral IGF-1 injection.

A single central injection of IGF-1 following an asphyxial insult in the adult rat was associated with a marked improvement in outcome as assessed histologically. Thus, in this model of hypoxic-ischemic encephalopathy IGF-1 and IGFBP-3 are induced in the region of damage and exogenous IGF-1 when administered intracerebroventricularly improves outcome.

Experiment B

Because of the potential application of these therapies which are effective following the insult, further studies were undertaken to clarify the mode of action and effects of central IGF-1 and insulin treatment after hypoxic-ischemic injury. These were performed firstly to determine the dose response characteristics of IGF-1 treatment, secondly to determine whether the neuroprotective effects were mediated via the insulin or type 1 IGF receptor and thirdly to clarify the relationship between IGF-1 administration and the time of insult. The effects of IGF-1 treatment on blood glucose and brain temperature were also evaluated.

These studies were approved by the Animal Ethical Committee of the University of Auckland. Adult male Wistar rats (52–66 day 280–320 g) were prepared under 3% Halothane/$O_2$ anaesthesia. The right side carotid artery was ligated. A guide cannula was placed an the dura 8.2 mm anterior from bregma and 1.4 mm from midline on the right. In selected rats a temperature transmitter (MINI-MITTER SM-FH-BP brain probe) was placed 5 mm from bregma on the dura of the ligated side. The cannula and transmitter were fixed in place with dental cement. Arterial blood samples were obtained via left ventricular heart puncture sampling before ligation and serum analyzed for glucose and lactate with a 230 Y glucose lactate analyzer (Yellow Springs Instrument Co, Inc, Ohio. For the preinsult treatment group whole blood was used for glucose and lactate measurements. The rats were allowed to recover from anaesthesia for 1 hour and were then placed in an incubator with humidity 85±5% and temperature 31±0.5° C. for 1 hour before hypoxia. Oxygen concentration was reduced and maintained at 6±0.2 $O_2$% hypoxia for 10 minutes. The rats were kept in the incubator for two hours after the hypoxia. An additional rat with a brain temperature probe was included in each group to record cortical temperature from 1 hour preinsult to 2 hours postinsult. Intraventricular injections were made at 1μ 1/minute under 1.5%–2% halothane anaesthetic. Rats in each treatment group were infused simultaneously. The rats had free access to food during experiment and were sacrificed at 120 hours after hypoxia with overdose of sodium pentobarbitol. The brain was prepared for histological analysis as previously described (Klempt et al. 1991). Briefly, the brain was perfused in-situ with FAM (Formaldehyde, Acetic Acid, Methanol 1:1:8) then paraffin embedded. The sections were stained with Thionin and Acid Fuchsin. The extent of neuronal loss was determined as described elsewhere (Klempt et al 1991). Briefly this was done via light microscopy by two independent assessors, one of whom was blinded to the experimental grouping. The percentage of dead neurons in the hippocampus, cortex and striatum were estimated within three sections from anterior to posterior. The percentage of dead neurons was scored as follows: 0: <10% 2: 10–50% 3: 50–90% 4: >90% 5: no surviving neurons. All brains were also scored for the presence or absence of cortical infarction, defined as a region of tissue death or parenchymal pan-necrosis due to death of glia as well as neurons. Rats dying before the end of the experiment were excluded from histological analysis.

1) Dose response: To clarify the dose response for IGF-1 response sixteen groups of 4 rats were treated with either 50, 5, 0.5 or 0 μg (vehicle) recombinant human-IGF-1 (Genentech, Inc., South San Francisco, Calif. 94080). The IGF-1 was given in a 20 μl bolus over 20 minutes. The vehicle was 0.1% bovine serum albumin (BSA) in 0.1M citrate diluted with sodium bicarbonate and phosphate buffered saline (PBS), pH7.3±0.05. The mean cortical temperature during hypoxia was 37.1±0.3° C. Seven animals died distributed across all treatment groups. The arterial serum glucose and lactate concentrations were measured 1 hour postinfusion for 50 μg IGF-1 and vehicle treated animals with a 230 Y glucose lactate analyzer (Yellow Springs Instrument Co, Inc, Ohio).

2) Specificity of action: To compare the effect of insulin with IGF-1 eighteen groups of 3 rats were treated either with 20 μg IGF-1, 20μ insulin (Eli Lilly, Indianapolis, USA) or vehicle. These were given in 10 μl over 10 minutes at 2 hours after the insult. Vehicle was 0.1M acetic acid diluted with 0.1% BSA dissolved in 0.15M PBS: both hormones were similarly diluted. One vehicle treated rat died.

3) Time of administration: To evaluate the effects of pre-insult administration 11 pairs of rats treated with 20 μg. recombinant human-IGF-1 or vehicle alone were studied. These were given as a 10 μl was given over 10 minutes. The vehicle was 0.1M acetic acid diluted with 0.15M PBS. One animal died during the experiment.

4) Brain temperature recordings: The temperature of the ipsilateral cortex was recorded during and for 20 hours after hypoxia in a separate group of 9 20 μg IGF-1 treated and 9 vehicle treated rats. IGF-1 or vehicle along was given at 2 hours after the hypoxia. Temperature was continuously measured via minimitter telemetric probes, averages were calculated and stored at one minute intervals (Dale et al. 1989). Recordings from 3 rats were rejected due to technical problems.

5) Statistics: MANOVA followed by application of protected least-significant -difference procedure for post-hoc comparisons were used to compare neuronal loss and physiologic parameters between groups. The neuronal loss scores were log transformed and region was a repeated measure. Infarction rate was compared using Fisher's exact test with the Bonferroni correction for multiple comparisons. Results are presented as mean±SEM.

Results

Figure 3:
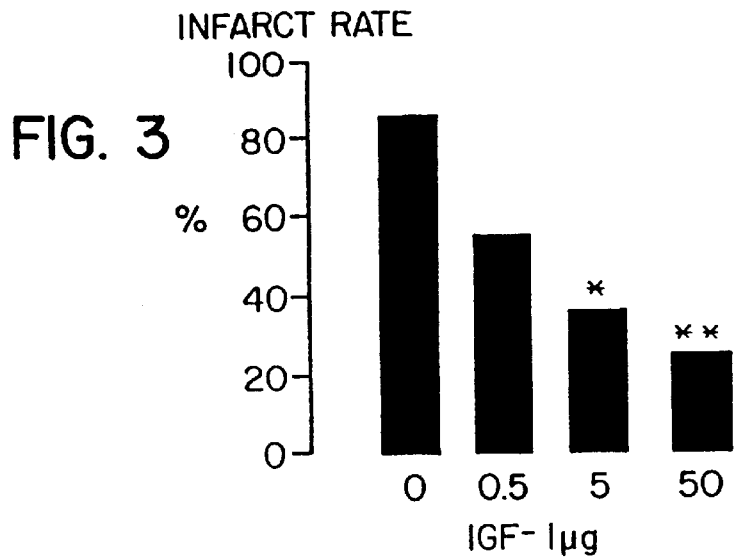
FIG. 3 shows infarction rate following treatment with 50 $\mu$g IGF-1 2 hours after the hypoxia. [The incidence of infarction was reduced following treatment with 5–50 $\mu$g IGF-1. $p<0.05$, **$p<0.01$]
Figure 4:
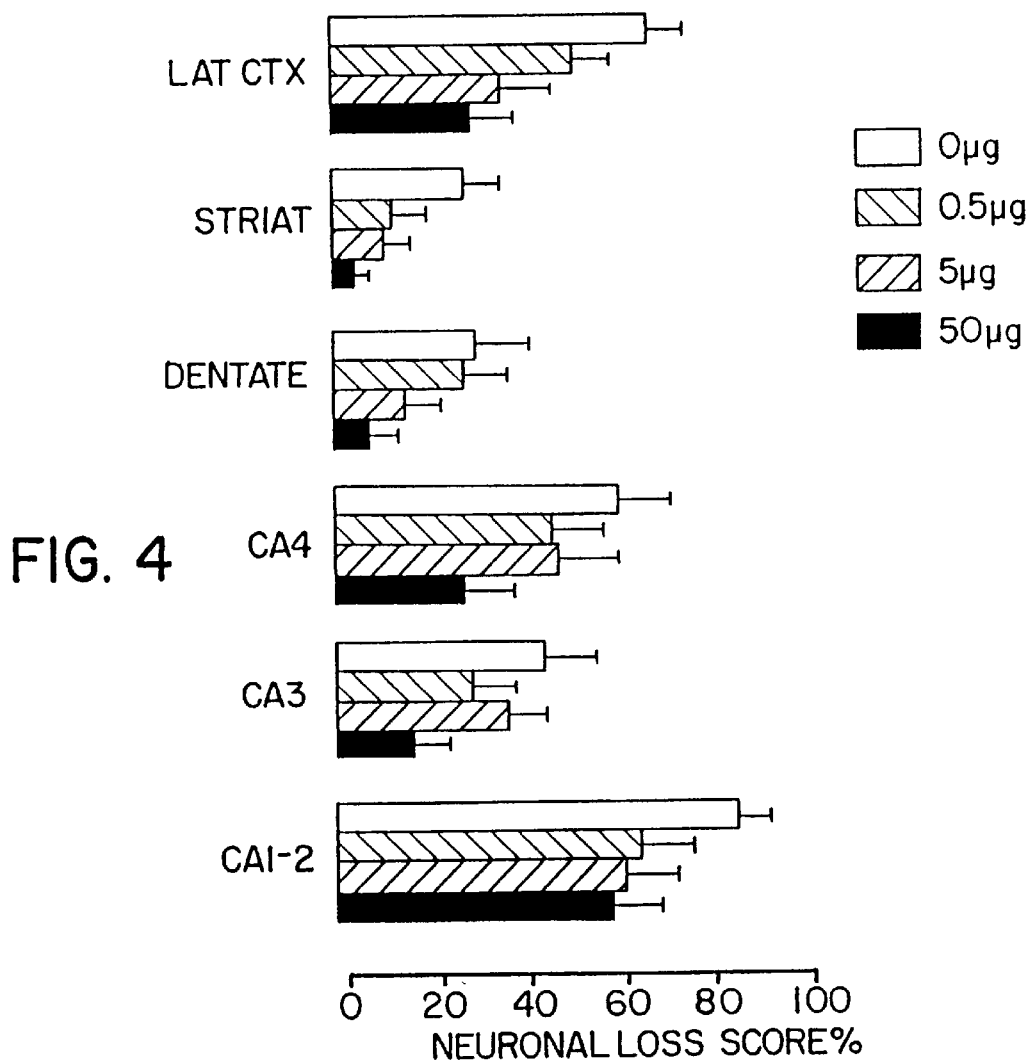
FIG. 4 shows regional neuronal loss scores following treatment with 0–50 $\mu$g IGF-1. [Overall neuronal loss was reduced following 50 $\mu$g ($p<0.01$)]

1) Dose response study: Five days after hypoxia neuronal loss was widespread within the middle cerebral artery territory of the ligated hemisphere of vehicle treated controls. The was extensive loss of neurons and infarction with the lateral cortex, hippocampus and striatum. Five to 50 μg IGF-1 reduced (p<0.05) the incidence of infarction in a dose dependent manner (FIG. 3). In all regions of the damaged hemisphere there was a dose dependent reduction in neuronal loss (p<0.01) (FIG. 4). Treatment with 50 μg IGF-1 did not effect serum glucose concentrations (8.8±0.2 mM/1) compared to vehicle treated controls (8.7±0.2 mM/1) measured one hour after infusion.

Figure 5:
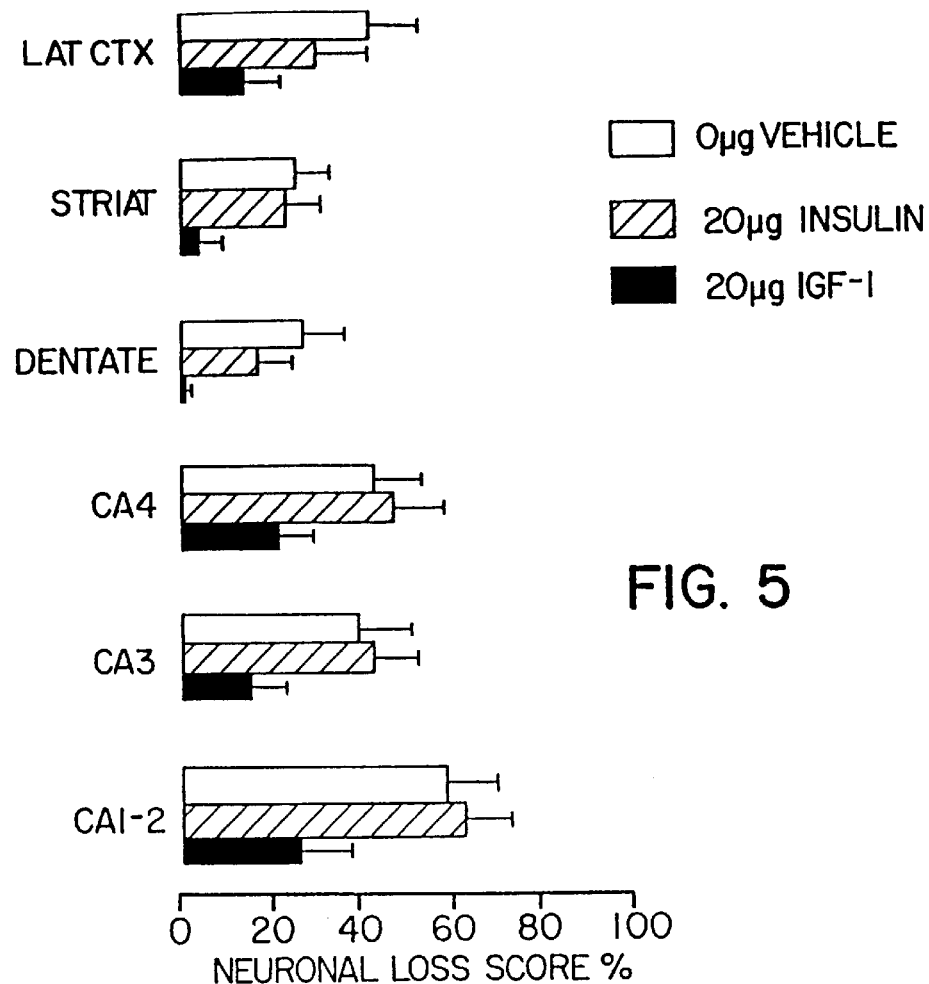
FIG. 5 is a comparison of regional neuronal loss scores following treatment with equimolar concentrations of insulin, IGF-1 and vehicle 2 hrs following injury. (IGF-1 improved outcome compared to insulin ($p<0.05$))
Figure 6:
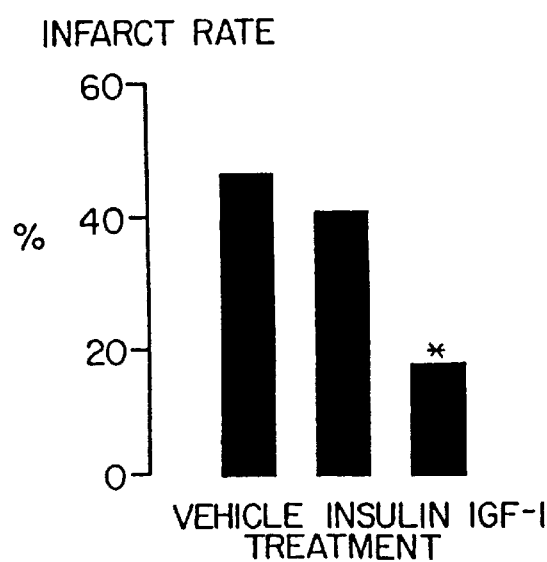
FIG. 6 shows infarction rate following treatment with equimolar doses of insulin, IGF-1 or vehicle 2 hrs following injury. [IGF-1 reduced the infarction rate compared to vehicle ($p<0.05$)]

2) Specificity: IGF-1 treatment improved overall histological outcome compared to insulin (p<0.05) (FIG. 5). Only IGF-1 treatment reduced the infarction rate (p<0.05) (FIG. 6).

Figure 7:
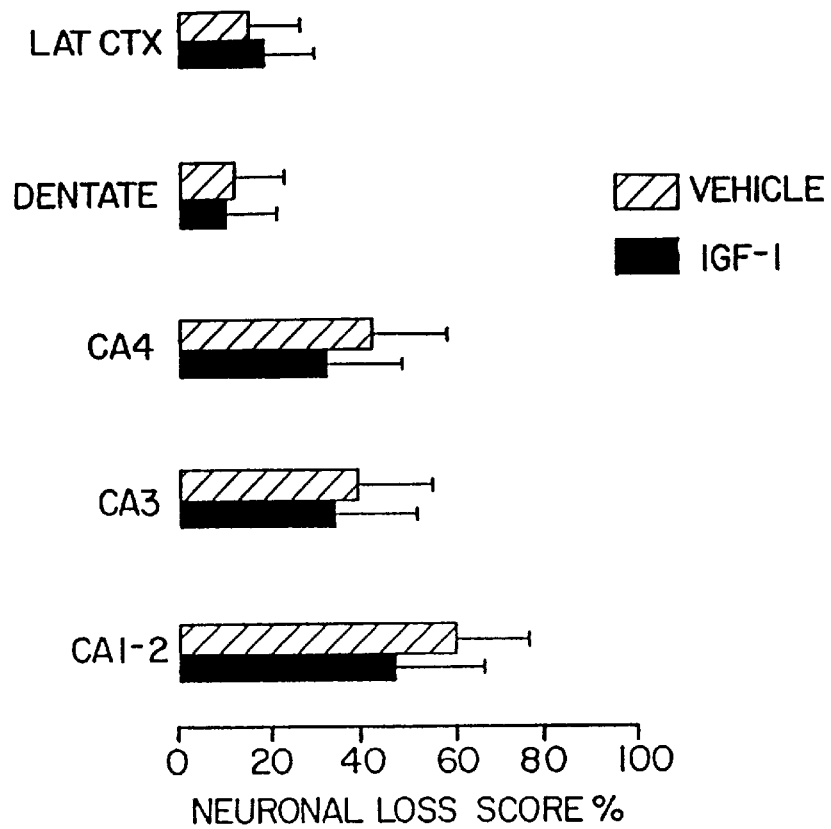
FIG. 7 shows the effect of administration of 20 $\mu$g IGF-1 given one hour before hypoxia (treatment did not significantly alter outcome)

3) Timing: in contrast to postasphyxial administration of 20 μg IGF-1 in the previous experiment. Histological outcome was not significantly different between vehicle and IGF-1 groups treated 1 hour before hypoxia (FIG. 7).

Figure 8:
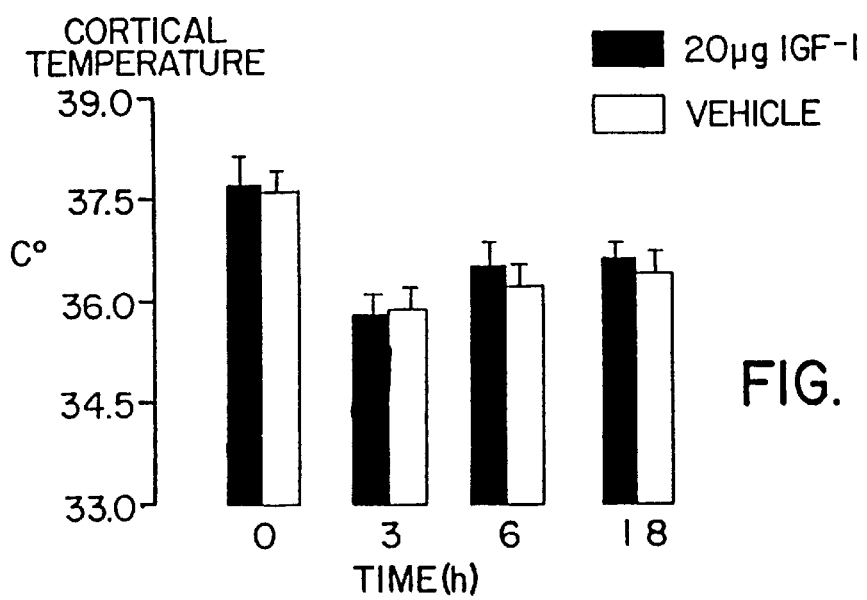
FIG. 8 shows the effect of treatment with IGF-1 on recovery of cortical temperature. These measurements were made during and after the hypoxia from the injured hemisphere. Treatment did not significantly alter brain temperature.

4) Brain temperature: IGF-1 treatment (n=7) after hypoxia did not significantly alter cortical temperature compared to vehicle treated controls (n=8) (FIG. 8).

Table 1 describes the preinsult status of each treatment group.

Discussion of Experiment B

Type 1 IGF receptors occur throughout the CNS on both neurons and glia with the highest density in the striatum and cortex (Lesniak et al 1988; Hill et al 1986). IGF-1 treatment reduced neuronal loss in all regions studied. This treatment also lowered the incidence of infarction indicating that loss of glial cells was reduced. These results agree with in vitro studies that indicate IGF-1 has potent trophic nonselective actions on neurons (Knusel at al 1990). Insulin has a much lower affinity for IGF receptors competing with IGF-1 only when at 100-fold higher concentrations (Gilmour et al 1988). Thus our results indicate that the neuroprotective effects, occur via IGF receptors (see FIG. 5). It is likely that the previously reported neuroprotective effects of insulin occur via the type 1 IGF receptor.

Many previously described neuroprotective strategies have been found to be indirectly effective by inducing hypothermia (Buchan, Pulsinelli, 1990). A lowering of cortical temperature as little as two degree can improve outcome (Bustom at al 1987). IGF-1 treatment did not alter cortical temperature excluding this possibility (see FIG. 8). IGF-1 when given in high doses systemically that saturates the IGF binding proteins is hypoglycaemic. Some studies suggest that hyperglycaemia can worsen outcome by increasing lactate accumulation and it is possible that a hypoglycaemic effect may be protective. However, central IGF-1 treatment did not significantly effect systemic glucose concentrations at the doses used. Thus a hypoglycaemic mechanism if unlikely.

IGF-1 given one hour before hypoxia did not alter outcome (see FIG. 7). Rat CSF is turned over about every 2 hours and the half life of IGF-1 is likely to be short due to tissue uptake. The lack of effect may be due to rapid turn over of IGF-1 leaving little activity following injury. Movement of peptides from the cerebrospinal fluid (CSF) into the brain parenchyma are generally thought to occur by simple diffusion. This process leads to very steep (1000 fold) concentration gradients over relatively short distances of one millimeter into the parenchyma (Pardridge, 1991). Given the greatly differing depths of the structures effected by treatment it is unlikely that IGF-1 is moving by simple diffusion alone (see FIGS. 4 and 5). As the asphyxial brain changes the pattern of expression of IGF binding proteins with increased expression of IGFBP-2 and BP-3 and inhibition of BP-1 (Gluckman et al 1992; Gluckman et al 1991), it may be that it is the expression of binding proteins that alters the kinetics of IGF distribution.

TABLE 1

| GROUP | PREINSULT STATUS | | | |
|---|---|---|---|---|
| | MASS | LACTATE | GLUCOSE | n |
| Vehicle | 285 ± 5 | 1.4 ± 0.1 | 7.9 ± 0.6 | 15 |
| 0.5 μg IGF-1 | 297 ± 6 | 1.6 ± 0.1 | 8.4 ± 0.3 | 13 |

TABLE 1-continued

| | PREINSULT STATUS | | | |
|---|---|---|---|---|
| GROUP | MASS | LACTATE | GLUCOSE | n |
| 5 μg IGF-1 | 296 ± 5 | 1.5 ± 0.1 | 8.5 ± 0.2 | 14 |
| 50μ IGF-1 | 287 ± 5 | 1.4 ± 0.1 | 8.1 ± 0.4 | 15 |
| Vehicle | 293 ± 3 | 1.4 ± 0.1 | 9.0 ± 0.1 | 17 |
| 20 μg IGF-1 | 291 ± 5 | 1.6 ± 0.1 | 9.5 ± 0.2 | 18 |
| 20 μg Insulin | 293 ± 4 | 1.5 ± 0.1 | 9.2 ± 0.2 | 18 |
| Pre Vehicle | 298 ± 4 | 1.5 ± 0.2 | 5.9 ± 0.3 | 11 |
| Pre 20μg IGF-1 | 300 ± 2 | 1.7 ± 0.2 | 6.4 ± 0.2 | 10 |

Summary of Experiments

Recombinant human IGF-1 (in these experiments, dissolved in 0.5 m acetic acid at 20 μg/10 μl subsequently, diluted 9 times with 0.15M phosphate buffered saline to give a pH of about 7.3) administered in a single dose given in the period commencing with the time of the CNS injury or insult through to about 8 hours thereafter (and including a time point of about 2 hours after the neural insult) has shown therapeutic effect in reducing or eliminating the severity of CNS damage suffered after a neural insult. IGF-1 is especially useful in reducing infarction, and loss of glial cells and non-cholinergic neuronal cells associated with neural injury.

Thus it can be seen that in at least the preferred forms of the invention a method and/or medicament for treating CNS damage is provided which is able to substantially prevent or treat CNS damage. CNS damage may be associated with asphyxia, hypoxia, toxins, infarction, ischemia or trauma. It will be appreciated that the main application of the invention is to humans. However, the usefulness of the invention is not limited thereto and treatment of other non-human animals, especially mammals, is also within the scope of the invention.

The present invention, therefore, recognises the role of an administration of a medicament comprising IGF-1 and/or other compounds of similar effect into a patient at or following a CNS insult with the consequential result that CNS damage is minimised by preventing the otherwise consequential, self-induced damage that would occur following the injury, ie. it is not involved with the repair of damage that has already occurred but to a treatment at, or subsequent, to the injury but before the consequential long term damage occurs thereby minimising the occurrence of such damage.

What is claimed is:

1. A method of treating neural damage suffered after a CNS insult affecting glia or other non-cholinergic cells in a mammal, comprising administering to the central nervous system of said mammal a medicament comprising an effective amount of IGF-1 and/or a biologically active analog of IGF-1.

* * * * *